United States Patent
Verma et al.

(10) Patent No.: US 9,510,800 B2
(45) Date of Patent: Dec. 6, 2016

(54) METHOD AND APPARATUS FOR REDUCING MOTION INDUCED BLUR IN MEDICAL IMAGES USING TIME GATE PROCESSING

(71) Applicant: Siemens Medical Solutions USA, Inc., Malvern, PA (US)

(72) Inventors: Shiv Shanker Verma, Knoxville, TN (US); Tobias Wenig, Kersbach (DE); Matthew Mitchell, Knoxville, TN (US)

(73) Assignees: Siemens Medical Solutions USA, Inc., Malvern, PA (US); Siemens Healthcare GmbH, Erlangen (DE)

( * ) Notice: Subject to any disclaimer, the term of this patent is extended or adjusted under 35 U.S.C. 154(b) by 137 days.

(21) Appl. No.: 14/596,249

(22) Filed: Jan. 14, 2015

(65) Prior Publication Data
US 2015/0206288 A1    Jul. 23, 2015

Related U.S. Application Data

(60) Provisional application No. 61/930,631, filed on Jan. 23, 2014.

(51) Int. Cl.
G06K 9/00 (2006.01)
A61B 6/00 (2006.01)
A61B 6/03 (2006.01)

(52) U.S. Cl.
CPC .............. *A61B 6/5235* (2013.01); *A61B 6/032* (2013.01); *A61B 6/037* (2013.01); *A61B 6/5288* (2013.01); *A61B 6/503* (2013.01); *A61B 6/5205* (2013.01)

(58) Field of Classification Search
None
See application file for complete search history.

(56) References Cited

U.S. PATENT DOCUMENTS

| 8,060,177 B2 | 11/2011 | Hamill | |
|---|---|---|---|
| 2012/0230556 A1* | 9/2012 | Wollenweber | G06T 11/008 382/128 |
| 2013/0085375 A1 | 4/2013 | Hamill | |

* cited by examiner

*Primary Examiner* — Hadi Akhavannik

(57) ABSTRACT

A first gate data representing a first plurality of time gates for a first medical imaging modality (e.g., PET or CT) is provided. The first plurality of time gates are based on a plurality of cycles of an acquired physiological signal of a person. A gate width is determined for a second medical imaging modality (e.g., CT or PET). A second gate data is generated, representing a second plurality of time gates for the second medical imaging modality. Each time gate in the second plurality of time gates has the determined gate width and is generated dependent on a respective time gate in the first plurality of time gates.

18 Claims, 11 Drawing Sheets

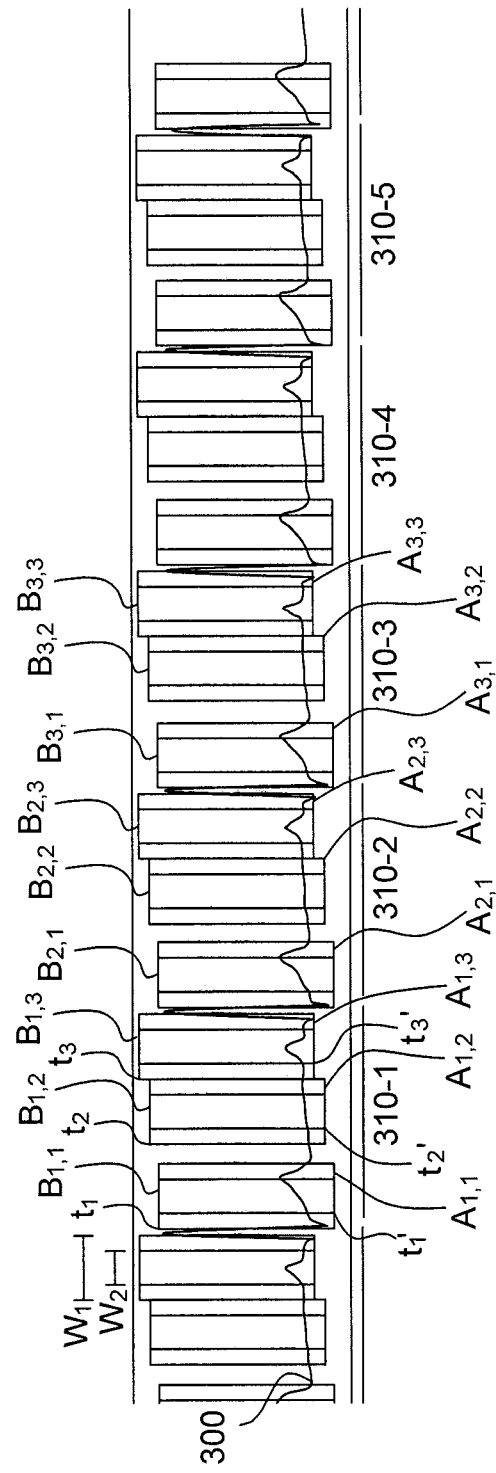

METHOD AND APPARATUS FOR REDUCING MOTION INDUCED BLUR IN MEDICAL IMAGES USING TIME GATE PROCESSING

CROSS-REFERENCE TO RELATED APPLICATION

This application claims priority under 35 U.S.C. §119(e) from U.S. Provisional Application Ser. No. 61/930,631 filed Jan. 23, 2014, the entirety of which is hereby incorporated by reference herein.

FIELD

Aspects of the present disclosure relate in general to processing data for medical imaging, and more particularly to techniques for reducing motion induced blur in medical images by intelligent processing of time gates related to gated scans.

BACKGROUND

Computed tomography (CT) scanning and positron emission tomography (PET) scanning are known methods for diagnostic medical imaging. CT scanning employs multiple X-ray images taken in multiple directions (i.e., with a scanner situated in different orientations relative to a patient) to generate a 3-dimensional image or multiple tomographic image slices. PET scanning employs a gamma-emitting radiopharmaceutical ingested by a patient or injected into a patient. Multiple gamma ray images are taken in multiple directions to generate a 3-dimensional PET image or multiple slices. CT and PET scanning provide different information. For example, CT scanning generally has higher resolution and is superior for providing structural data such as the structure of bones, organs, etc. PET scanning generally has lower resolution but provides more useful information regarding the functional condition of body tissues and systems such as the cardiovascular system. PET is superior for indicating the presence of soft tissue tumors or decreased blood flow to certain organs or areas of the body, for example. The complementary strengths of CT and PET scanning can be provided simultaneously by performing both methods in a single apparatus and imaging session. However, combining CT and PET scanning presents technical challenges because CT and PET require different scan times and have different sensitivities to patient motion.

PET scanning requires a relatively long duration data acquisition period, on the order of several minutes (e.g., about 30 minutes) for a typical clinically sufficient image. Typically, a large number of PET data acquisitions are acquired at many different angles during this period. Consequently, patient movement is a problem in PET scanning. Excessive motion of a patient can result in scan failure. Thoracic cage movement caused by breathing is a significant problem in PET scanning. By comparison, CT scanning is relatively fast and can typically be performed during one breath-hold by a patient.

Fusion of CT and PET images (i.e., PET-CT or CT-PET imaging) often is inaccurate because of inevitable patient movement and breathing. Associated problems include several types of CT artifacts, errors in the association between anatomy and PET uptake, motion blur in PET, and quantitative PET errors such as miscalculation of the standard uptake value due to underestimation or overestimation of attenuation.

Gated scanning has addressed some issues related to motion blur. Gated scanning is described in U.S. Pat. No. 8,060,177 to Hamill and U.S. Patent Publication 2013/0085375 to Hamill et al., the entirety of which applications are hereby incorporated by reference herein. Gated scanning (e.g., gated PET or gated CT) involves identifying and exploiting a physiological signal (e.g., respiratory or cardiac signal) that is cyclical in nature. Based on measuring such a physiological signal, the motion of an appropriate organ (e.g., lung or heart) can be determined during an acquisition. This information can be used to detect time intervals (referred to as gates, time gates, or time windows) of relatively little organ motion. Various gating algorithms (various ways to determine the gates) are known. Image creation (reconstruction) can then be restricted to using data (e.g., amplitude data) corresponding to the times within the time gates, such that the time gates are basically filters in the time domain. In particular, one or more time gates may be assigned per cycle of the physiological signal, and similarly situated gates in respective cycles can be used to reconstruct a dataset.

An example of gating is shown in FIG. 1. In FIG. 1, a plot of a cardiac signal 100 includes multiple cycles, where a cycle may be defined, e.g., from one R-peak to the next R-peak. R-peak refers to the R portion of the QRS complex, which is a series of three graphical deflections in a cardiac signal. Eight complete cycles 110-1, . . . , 110-8 are shown in this example. FIG. 1 shows a 4-gated scan example with gates labelled 1, 2, 3, and 4 that span the entire cycle and that do not overlap one another. In other gating examples, gates may not span an entire cycle or may overlap one or more other gates within a cycle. For visualization purposes, gates 1, 2, 3, and 4 are shown in FIG. 1 as rectangles at different vertical displacements (i.e., like an ascending staircase), but the gates may be just the one-dimensional time intervals corresponding to those rectangles. As shown in FIG. 1, the same pattern of gates occurs in each cycle. To avoid visual clutter, the gates are not designated with reference numerals in each cycle in FIG. 1 but are instead labelled only within cycle 110-4. All gates having the same gate number can be used to reconstruct a dataset that has less motion blur than would occur without gating.

Although gating based on a cardiac signal is shown in FIG. 1, gating may be based on other cyclical physiological signals. For example respiratory gating may be a performed with a respiratory signal, for which a cycle may be defined from an inspiration peak to the next inspiration peak.

Even with gated scanning, there remain problems with motion blur, particularly when gated scans of two different imaging modalities (e.g., PET and CT) are used. Additionally, the problem of two separate motions (heart motion due to heartbeat and lung motion due to breathing) causing blur in the cardiac imaging scenario has remained challenging even with gating.

SUMMARY

In some embodiments of the present disclosure, a method of processing data for medical imaging includes providing a first gate data representing a first plurality of time gates for a first medical imaging modality (e.g., PET or CT). The first plurality of time gates are based on a plurality of cycles of an acquired physiological signal of a person. A gate width is determined for a second medical imaging modality (e.g., CT or PET). A second gate data is generated, representing a second plurality of time gates for the second medical imaging modality. Each time gate in the second plurality of time gates has the determined gate width and is generated dependent on a respective time gate in the first plurality of time gates.

In some embodiments, a method of processing data for medical imaging includes providing a first gate data representing a first plurality of time gates for a medical imaging modality (e.g., PET). The first plurality of time gates are based on an acquired cardiac signal of a person. The method further includes providing a second gate data representing a second plurality of time gates for the medical imaging modality. The second plurality of time gates are based on an acquired respiratory signal of the person. A third gate data is generated, representing a third plurality of time gates formed by an intersection of the first and second pluralities of time gates. A visualization of at least one of the time gates in the third plurality of time gates is displayed on a screen to a user.

In some embodiments, a non-transitory computer readable medium has instructions embodied tangibly thereupon, the instructions when executed configured to cause one or more processors to perform the operations of one or both of the above-described methods of processing data for medical imaging.

BRIEF DESCRIPTION OF THE DRAWINGS

The following will be apparent from elements of the figures, which are provided for illustrative purposes and are not necessarily to scale.

FIG. 3 is an illustration showing CT gates centered relative to respective PET gates in accordance with some embodiments.

DETAILED DESCRIPTION

This description of the exemplary embodiments is intended to be read in connection with the accompanying drawings, which are to be considered part of the entire written description.

Various embodiments of the present disclosure address the foregoing challenges associated with motion blur in medical images, e.g., by leveraging the technique of gating in new ways with intelligent processing of gate data.

Figure 1:
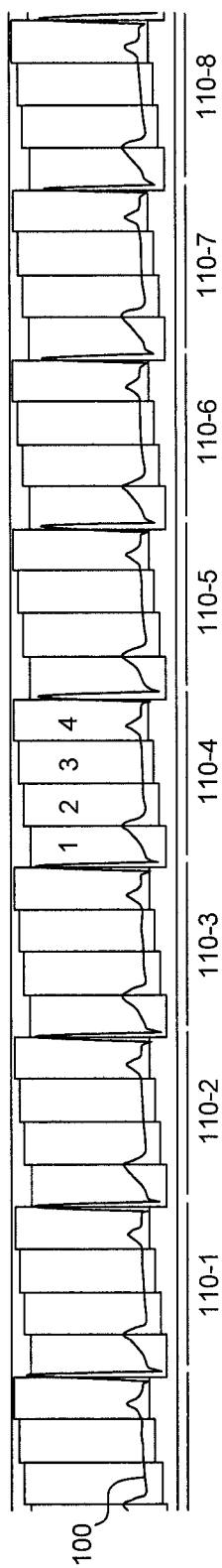
FIG. 1 is an illustration showing an example of cardiac gating.
Figure 2:
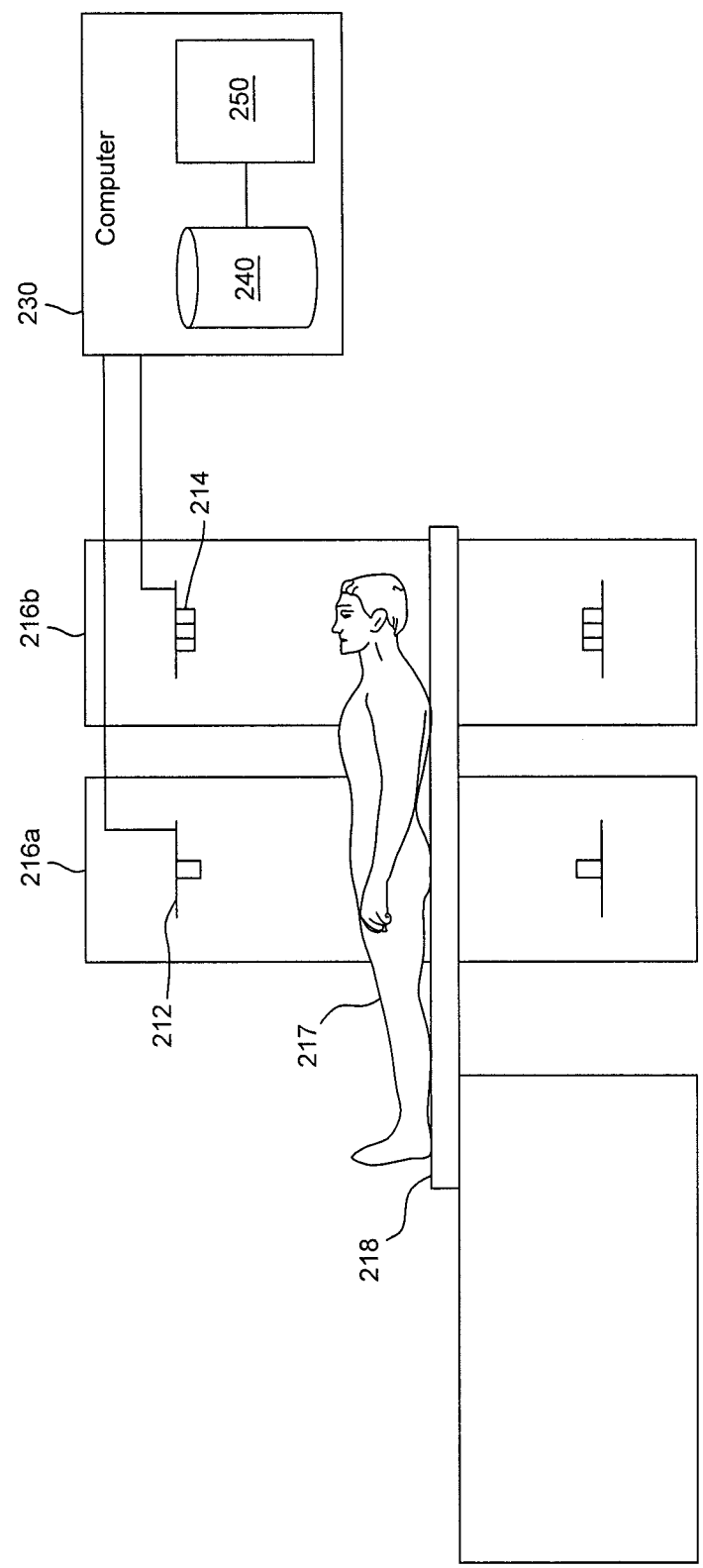
FIG. 2 is an illustration of one example of a combination PET/CT apparatus that may be used with various embodiments of the present disclosure.

FIG. 2 shows one example of a dual imaging modality apparatus (e.g., combination PET/CT apparatus) 200 that may be used with various embodiments. PET and CT are described herein as examples of first and second imaging modalities that may be used in various embodiments, but they are non-limiting examples. The apparatus 200 includes a scanner for a first imaging modality (e.g., CT scanner) 212 provided in a gantry 216a and a scanner for a second imaging modality (e.g., PET scanner) 214 provided in a gantry 216b. A patient 217 lies on a movable patient bed 218 that may be movable between the gantries. Alternatively, the scanners 212 and 214 may be combined together in a single gantry.

Scan data from the first and second imaging modalities are stored at one or more computer databases 240 and processed by one or more computer processors 250 of a computer 230. Scan data from the first and second imaging modalities may be stored in the same database 240 or in separate databases. The graphical depiction of computer 230 in FIG. 2 is provided by way of illustration only, and computer 230 may include one or more separate computing devices.

In one embodiment, the first and second imaging modalities are PET and CT, respectively. A patient is scanned using CT and PET imaging to yield CT acquisition and physiological waveform data and PET acquisition and physiological waveform data, respectively. The scans may be performed sequentially, with a PET scan following a CT scan. In another embodiment, the first imaging modality is CT and the second imaging modality is PET. For the first imaging modality (e.g., PET), gating is performed based on an acquired physiological signal to determine gate locations (in time) and a width (in time duration) for the PET gates. Any gating algorithm known in the art can be used for this purpose. Gate width (the time duration of a gate) depends on the imaging modality. The widths (time durations) of respective gates in a cycle may be constant or may vary, e.g., depending on the gating algorithm that is used and the constraints of the imaging modality. A PET gate width is typically larger (wider) than a CT gate width because PET preserves and uses more data. CT gate width is based on rotation time and is usually smaller (narrower) than PET gate width to allow for better time localization.

For the second imaging modality (e.g., CT), the gate width is determined, but the gates are not placed according to traditional gating algorithms. Rather, continuing the above example, the CT gates are placed in a manner dependent on respective PET gates, e.g., by centering each CT gate relative to a corresponding PET gate.

For example, referring to FIG. 3, performing gating for PET with cardiac signal 303 yields PET gates $A_{1,1}, A_{1,2}, A_{1,3}$ having a gate width $w_1$ and gate start times $t_1$, $t_2$, and $t_3$. Similarly, PET gates $A_{2,1}, A_{2,2}, A_{2,3}, A_{3,1}, A_{3,2}, A_{3,3}$, etc. are determined for cycles 310-2, 310-3, etc. The gate locations may be stored (e.g., in a memory) in various formats, as discussed further below in the context of gating modes. Traditionally, gates for the other modality (CT in this example) would be determined according to a gating algorithm in a manner that is independent of the PET gates. In contrast, in various embodiments of the present disclosure, the CT gates are placed in a manner that is dependent on the existing PET gate placements. For example, the CT gates may be centered relative to respective PET gates, as shown in FIG. 3.

Various algorithms may be used to center-align the CT gates with the existing PET gates. For example, the CT gate width $w_2$ may be determined based on the imaging modality (here, CT), and the start time for each CT gate may be determined according to the following formula:

$$t_{CT} = t_{PET} + (w_1 - w_2)/2, \quad (1)$$

where $t_{PET}$ is the start time of a previously-determined PET gate, $t_{CT}$ is the calculated start time of the corresponding CT gate, $w_1$ is the PET gate width, and $w_2$ is the CT gate width.

One of ordinary skill in the art recognizes that to implement center-alignment, formulas other than (1) may instead be used, e.g., based on gate midpoint in some embodiments.

Thus, CT gates $B_{1,1}$, $B_{1,2}$, $B_{1,3}$, etc. with gate start times $t_1'$, $t_2'$, $t_3'$, etc. may be generated in a manner that center-aligns them with respective PET gates; for convenience, this set of CT gates may be referred to as $X_{CT}$.

In some embodiments, CT gate placement may be performed according to a different fixed relationship (different than center-alignment) relative to existing PET gates. For example, CT gate placement may be biased within the existing PET gates to the sub-phase with the most motion, thereby yielding a potentially better attenuation correction map. Such an alternative CT gate placement technique may be useful in the situation where the PET gate is wide and is centered at an inspiration or expiration peak.

In some embodiments, gate parameters corresponding to the gates in set $X_{CT}$ are determined and stored. Gate parameters are discussed in further detail below.

In some embodiments, a different fixed relationship between the CT gates and the existing PET gates may be used. For example, the start time for each CT gate in set $X_{CT}$ may alternatively be determined according to the following formula:

$$t_{CT} = t_{PET} + (w_1 - w_2)/2 + \epsilon, \quad (2)$$

where $\epsilon$ is any a positive or negative number and the other variables in formula (2) are the same as in formula (1).

In some embodiments, the time duration between (a) the start time of each CT gate occupying a similar phase within respective cycles and (b) the start time of the corresponding cycle is determined, and those time durations are averaged across multiple cycles (e.g., all cycles of available data). In other words, the start time of each CT gate occupying a similar phase is considered as a time offset relative to the start of the cycle (i.e., intracycle start time offset), and these intracycle start time offsets are averaged to yield an average intracycle start time offset. Referring back to FIG. 3, a pattern of three CT gates is observed within each cycle: $B_{1,1}$, $B_{1,2}$, $B_{1,3}$, then $B_{2,1}$, $B_{2,2}$, $B_{2,3}$, then $B_{3,1}$, $B_{3,2}$, $B_{3,3}$. Thus, gates $B_{1,1}$, $B_{2,1}$, $B_{3,1}$, etc. occupy a similar phase within respective cycles and may be referred to as phase-similar gates with respect to the cycles. Thus, the intracycle start time offsets {(start time of gate $B_{1,1}$)−(start time of cycle 310-1), (start time of gate $B_{2,1}$)−start time of cycle 310-2), . . . } may be averaged to yield an average intracycle start time offset that may be labeled $\delta_1$. This averaging is optional and does not need to be performed in some embodiments, e.g., when a simultaneous acquisition modality such as PET/MR is used.

Likewise, average intracycle start time offsets may be calculated for other groups of phase-similar CT gates. For example, the intracycle start time offsets {(start time of gate $B_{1,2}$)−(start time of cycle 310-1), (start time of gate $B_{2,2}$)−start time of cycle 310-2), . . . } may be averaged to yield an average intracycle start time offset $\delta_2$, and the intracycle start time offsets {(start time of gate $B_{1,3}$)−(start time of cycle 310-1), (start time of gate $B_{2,3}$)−start time of cycle 310-2), . . . } may be averaged to yield an average intracycle start time offset $\delta_3$.

In some embodiments, a set $Y_{CT}$ of CT gates having gate width $w_2$ and gate start times {(start time of cycle 310-1)+$\delta_1$, (start time of cycle 310-1)+$\delta_2$, (start time of cycle 310-1)+$\delta_3$, (start time of cycle 310-2)+$\delta_1$, (start time of cycle 310-2)+$\delta_2$, (start time of cycle 310-2)+$\delta_3$, etc.} is established. Gate parameters corresponding to the gates in set $Y_{CT}$ may be calculated and stored.

Gate parameters (also referred to as gating parameters) may be used to represent time gates (e.g., CT gates or PET gates) in various ways and may be stored for subsequent retrieval and processing (e.g., for the reconstruction of images based on gating). Gate parameters may be stored in any convenient data format, e.g., as a string or as a sequence of numbers. The particular gate parameters used may vary depending on the gating mode that is used. Various gating modes are known, and some of them are shown in FIGS. 4A-4D.

Figure 4A:
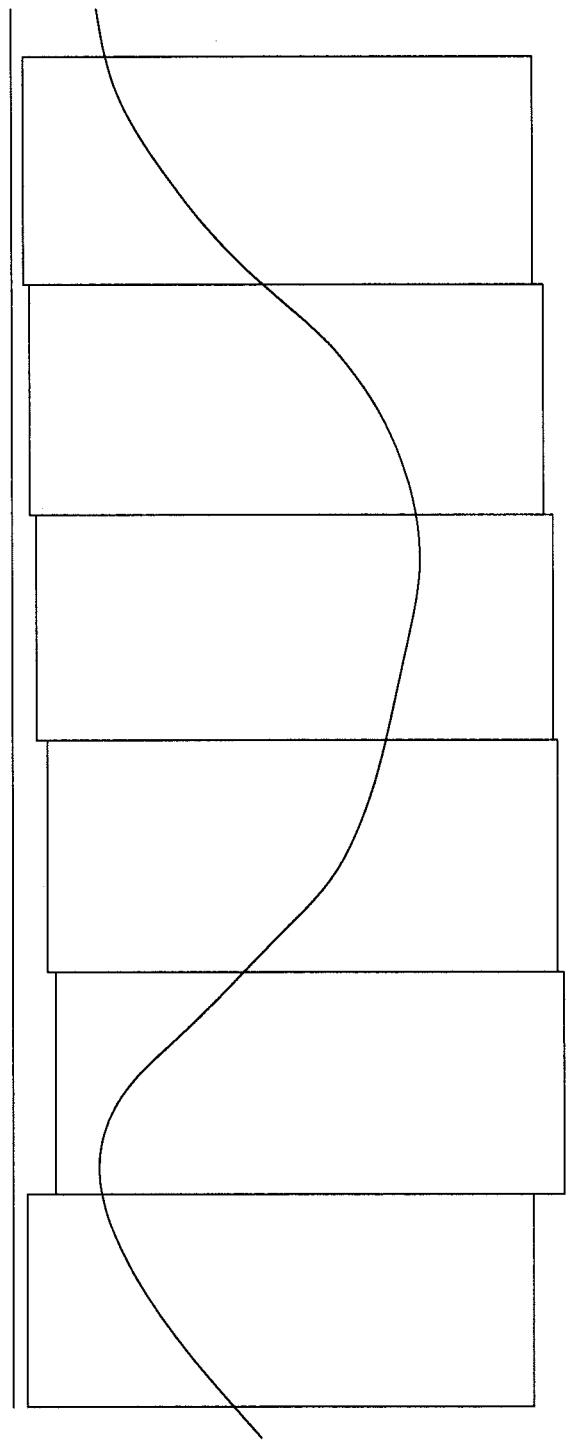
FIGS. 4A-4D are examples of gating modes. 4A: equal gates mode; 4B: percentage mode; 4C: multiphase mode (amplitude-based mode); 4D: time offset mode.

FIG. 4A corresponds to a gating mode referred to as equal gates mode. In this mode, a complete cycle of a physiological signal (respiratory signal in this example, although other physiological signals may be used instead) is split into multiple gates (here, five gates; any number of gates may be used) having an equal width and spanning the cycle (e.g., computed from one inspiration peak to the next inspiration peak) with no overlap. The gate parameters for this mode may be represented as: 1 G 2 G 3 G 4 G 5 G.

Figure 4B:
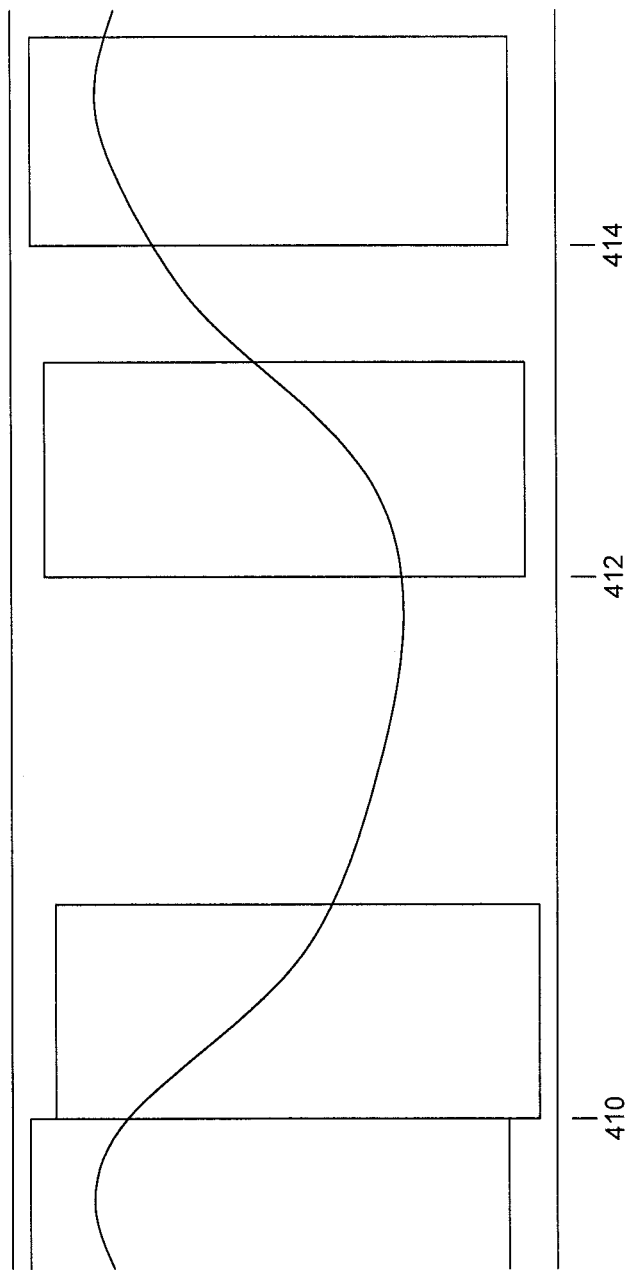

FIG. 4B corresponds to a gating mode referred to as percentage mode. In this example with three gates per cycle (more generally, any number of gates per cycle may be used), respective gates begin at 10% into a cycle (time point 410), 60% into a cycle (time point 412), and 90% into a cycle (time point 414). The gate parameters may be represented as: 10% 60% 90%. In this example, a respiratory signal is used for the gating, but other physiological signals may be used instead.

Figure 4C:
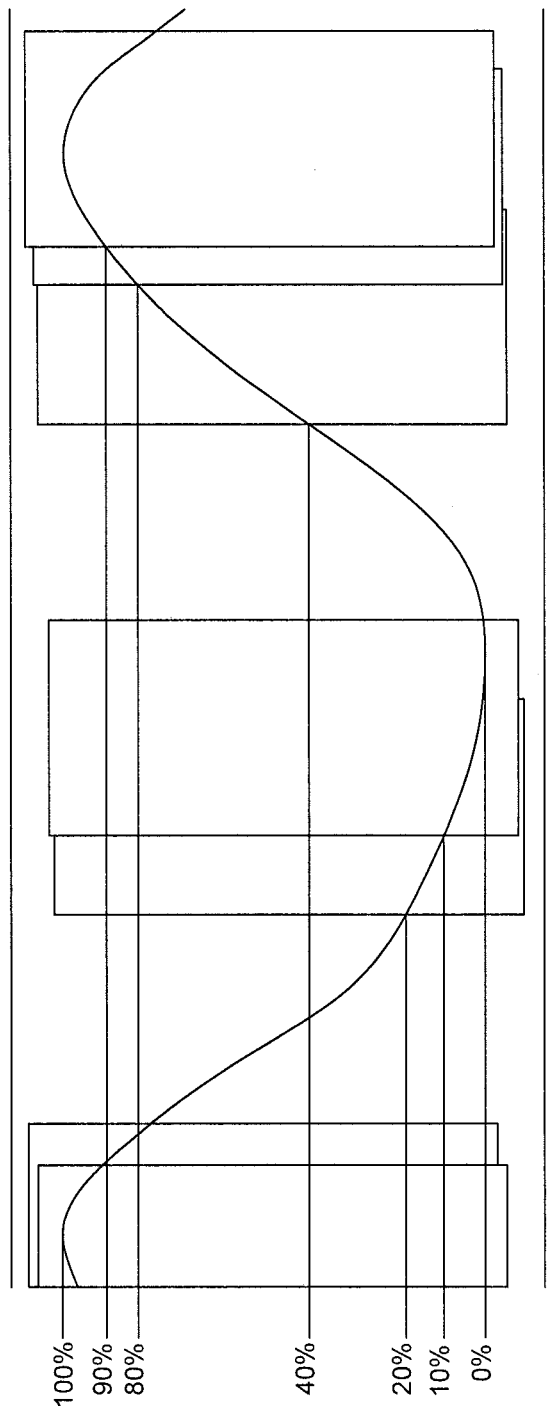

FIG. 4C corresponds to a gating mode referred to as multiphase mode or amplitude-based mode, where the gates are determined as a percentage of amplitude (e.g., of a respiratory signal) with an indication as to inspiration phase or expiration phase. Inspiration peak is at the maximum amplitude of the respiratory signal in FIG. 4C, expiration peak is at the minimum amplitude of that signal, inspiration phase is the phase (or sub-cycle) between an expiration peak and the next inspiration peak, and expiration phase is the phase (or sub-cycle) between an inspiration peak and the next expiration peak. Any number of gates may be used. In The gate parameters specifying gates in the example of FIG. 4C may be represented as: 20%_Ex 10%_Ex 40%_In 80%_In 90%_In. These parameters may be determined based on times (e.g., gate start times) by determining the amplitude value corresponding to a given gate start time.

Figure 4D:
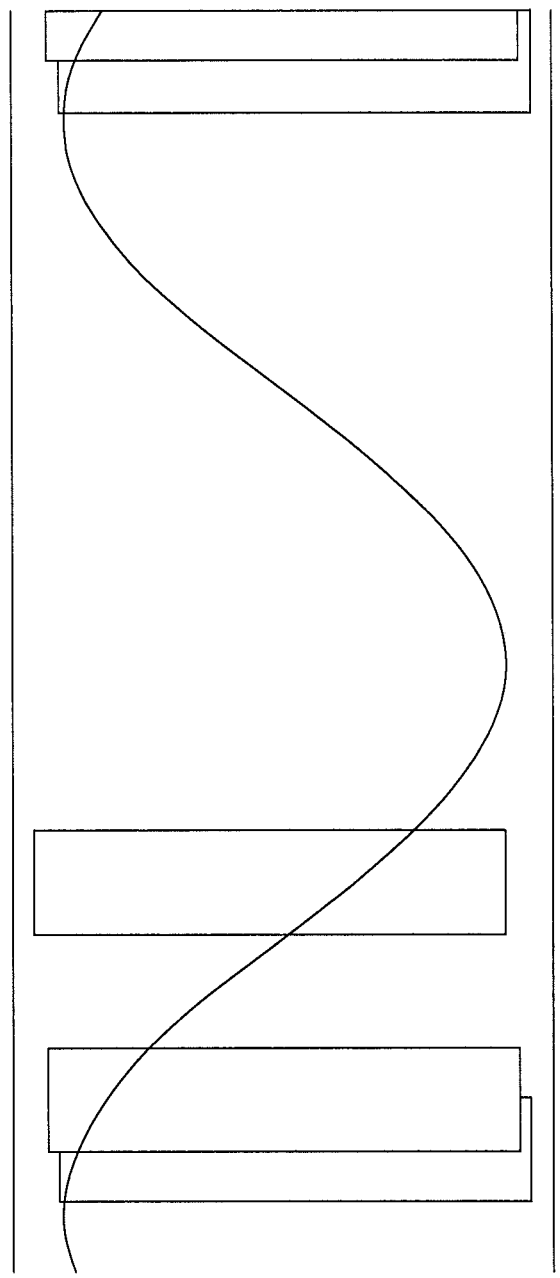

FIG. 4D corresponds to a gating mode referred to as time offset mode. In this mode, each gate is specified by its time offset (e.g., in milliseconds) relative to cycle start. For example, with three gates having time offsets relative to cycle start of 20 ms, 200 ms, and 1000 ms, respectively, the gate parameters may be represented as: 20 ms 200 ms 1000 ms. Although three gates per cycle and a respiratory signal are used for the gating, other numbers of gates per cycle and other physiological signals may be used instead.

In addition to the above-described gating modes, a mode referred to as optimal gating may be used. Optimal respiratory gating is described in, e.g., U.S. Patent Publication 2013/0085375 to Hamill et al.

The above-described procedures for generating CT gates (e.g., gates in set $X_{CT}$ or $Y_{CT}$) may be referred to generally as gate matching, as the CT gates are generated in a manner that matches them to the characteristics of existing (previously computed) PET gates, e.g., through a process that includes center-aligning. Gate matching may also be performed to match PET gates to the characteristics of existing CT gates. The labels $X_{CT}$ and $Y_{CT}$ used above are for convenience only in the context of the above example in which CT gates are generated dependent on PET gates; in an example where PET gates are generated dependent on CT gates, the labels may be $X_{PET}$ and $Y_{PET}$. More generally, gate matching may be performed to match the gates of one imaging modality to the characteristics of existing gates of another imaging modality, regardless of whether the gate width for the one imaging modality is narrower (smaller) or wider (larger) than the gate width for the other imaging modality.

In some embodiments, after set $X_{CT}$ or $Y_{CT}$ of gates is determined, the generated gates may be displayed to the user, e.g., using a user interface display such as FIG. 3. A prompt may be provided (e.g., on a screen) to prompt the user to confirm the matched gates ($X_{CT}$ or $Y_{CT}$ in the above example) or their gate parameters. Upon user acceptance, CT and PET images (more generally, images of two different imaging modalities) may be reconstructed. Image reconstruction for one imaging modality (e.g., PET, in the example above) may be performed by applying the PET gates to PET acquisition data (e.g., PET emission data) obtained from a PET scan of a person. In other words, only the PET acquisition data portions corresponding to the PET time gates are used for reconstruction. Image reconstruction for the other imaging modality (e.g., CT, in the example above) may be performed by retrieving (e.g., from a memory) stored gate parameters for a set of generated CT gates (e.g., set $X_{CT}$ or $Y_{CT}$ as above) and applying those CT gates to CT acquisition data (e.g., X-ray transmission data) obtained from a CT scan of the person. In some embodiments, a fusion image (e.g., PET-CT fused image) is generated based on the PET gates and CT gates. In various embodiments, medical images (e.g., CT, PET, or PET-CT images) that are generated based on the principles of gate matching (e.g., based on generating CT gates that are center-aligned with PET gates) exhibit reduced motion blur artifacts, and are thus sharper and have features that are easier to perceive visually, than images that are generated using traditional approaches.

Thus, automatic alignment of gates is available in some embodiments. By automating the placement of gates of one imaging modality relative to gates of another imaging modality, deterministic results are achieved, and the workflow is simplified (e.g., reducing the amount of manual user interaction). In some embodiments, after the initial gate matching (e.g., generation of PET gates and generation of CT gates matched to the PET gates), gate matching is continued whenever a change is made to the gates in one imaging modality. For example, if gate parameters are changed for one or more PET (or CT) gates (e.g., due to a user action or automated processing), then gate parameters for the CT (or PET) gates may automatically be updated to maintain the relationship between the CT and PET gates.

In some embodiments, a correction is applied after set $X_{CT}$ of CT gates is generated based on PET gates, to disambiguate generated CT gates that would otherwise be indistinguishable. For example, after applying formula (1) or (2) it may occur that due to rounding errors or other numerical computing issues there are two or more gates in set $X_{CT}$ that would have the same start time. In order to make such gates distinguishable from one another (so that, e.g., a user can see that they are different gates on a user interface), the parameters corresponding to some of the otherwise-indistinguishable gates may be adjusted. In general, if there are N distinct gates in a cycle for a first imaging modality (where N is an integer) and fewer than N distinct gates are generated for a second imaging modality dependent on (e.g., centered relative to) the gates of the first imaging modality, then sufficient gate parameters for the second modality are adjusted so that there will be N distinct gates for the second modality as well. For example, suppose that based on three PET gates in a cycle, CT gates having parameters 10%, 10%, and 20% are generated. To distinguish the gates from one another, a parameter for one of the first two gates may be adjusted to be, e.g., 9% or 11% (or any other small adjustment).

In some embodiments, a procedure referred to as dual gating may be used to reduce motion blur in cardiac images. For cardiac imaging (imaging the heart), two separate motions contribute to motion blur in images. Cardiac motion associated with the heartbeat and respiratory motion associated with breathing are both moving the heart all the time. For short acquisitions (e.g., for CT cardiac scanning) this is sometimes addressed by instructing the patient to hold his/her breath. This is not possible for a long running PET or PET-CT (also referred to as CT-PET) scan that can have a duration on the order of several minutes.

To overcome these limitations, dual gating may be used in some embodiments. Cardiac and respiratory signals are acquired simultaneously for PET. Then, both signals are gated (e.g., using any known gating algorithm), but only the overlap is used for image creation (reconstruction).

Figure 5:
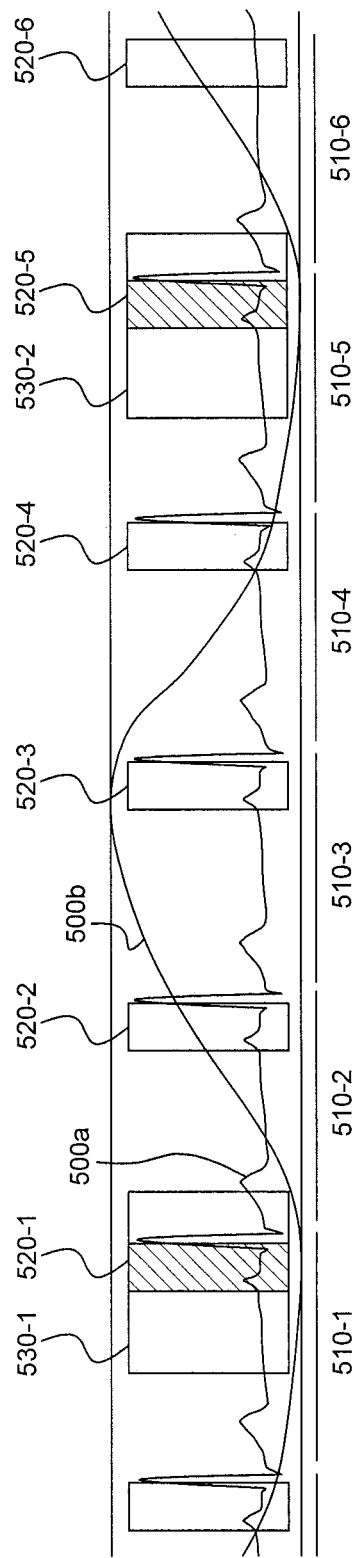
FIG. 5 is an illustration showing dual gating in accordance with some embodiments.

For example, referring to FIG. 5, cardiac signal 500a and respiratory signal 500b may be acquired for PET. Cycles 510-1, 510-2, . . . , 510-6 are shown corresponding to cardiac signal 500a, and approximately one cycle of respiratory signal 500b is shown. Both signals 500a, 500b are gated, yielding (in this example) gates 520-1, . . . , 520-6 based on cardiac signal 500a (these may be considered to form a set $G_C$) and gates 530-1 and 530-2 based on respiratory signal 500b (these may be considered to form a set $G_R$). The intersection of sets $G_C$ and $G_R$ (i.e., the intersection of the respective gates or time intervals from the cardiac gating and respiratory gating) is computed, and this intersection may be referred to as $G_I$. A visualization of at least one of the gates in the intersection set $G_I$ is displayed on a screen to a user. In the example of FIG. 5, intersection set $G_I$ is shown with diagonal striping.

In some embodiments, in addition to showing at least one of the gates in the intersection set $G_I$, the acquired cardiac signal 500a and respiratory signal and 500b are displayed (i.e., plotted) on the screen. The cardiac signal 500a and respiratory signal plots may be presented adjacent to one another or with one overlaid on the other (e.g., as shown in FIG. 5). The user may be prompted (via a user interface) to accept the gates in the intersection set $G_I$. Upon user confirmation, an image (e.g., PET image) may be reconstructed (created) using the gates in the intersection set $G_I$.

In some embodiments, the dual gating approach may be combined with cardiac matched gates (i.e., gating based on a cardiac signal) and CT scans for attenuation correction. In an example implementation of this approach, a dual gated PET acquisition is performed, the dual-gated reconstruction parameters for PET are configured, and then the respiratory phase that was used may be recorded and presented to the user. Then, the user (e.g., operator of the imaging equipment) can perform a cardiac CT scan with cardiac matching to the PET gates while instructing the patient to hold his/her breath at the respiratory phase that corresponds to the one that was calculated and recorded previously for the PET processing. Breath hold is possible for CT because of the shorter time duration for CT compared to PET. Instructing the patient to hold his/her breath in this way eliminates respiratory motion and thus simulates respiratory gates for the CT modality. In this way, PET and CT images may be generated that match in both the cardiac and respiratory phases even though simultaneous cardiac and respiratory gating cannot be performed for CT. If the CT scan data is acquired with a breath hold by the patient, optimal motion freeze of both motions (cardiac motion and respiratory motion) for both modalities (PET and CT) may be achieved.

Figure 6:
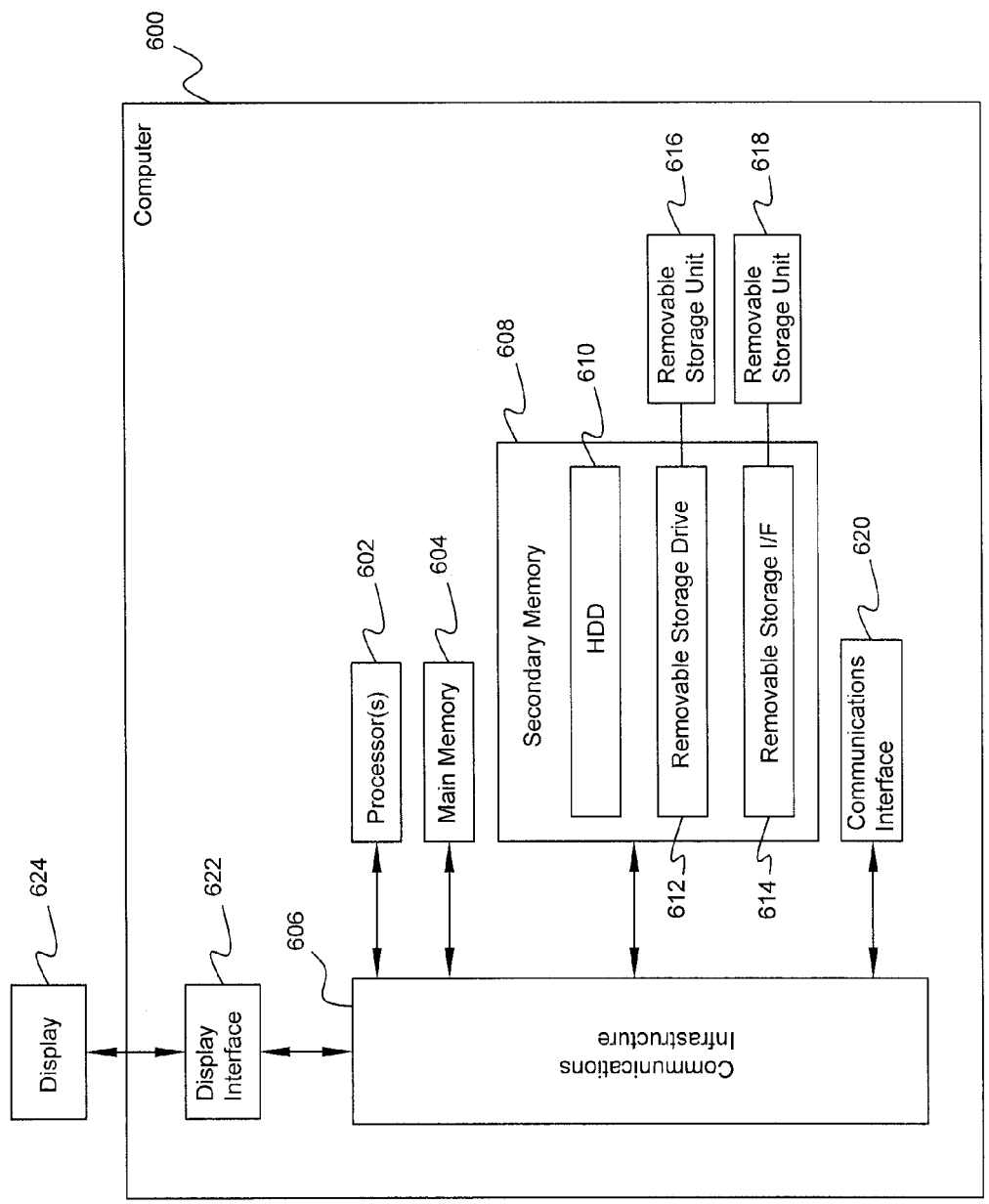
FIG. 6 is a block diagram of a computer system in accordance with some embodiments.

FIG. 6 is an architecture diagram of a computer 600 that may be used in some embodiments, e.g., for implementing computer 230 shown in FIG. 2. Computer system 600 may include one or more processors 602. Each processor 602 is connected to a communication infrastructure 606 (e.g., a communications bus, cross-over bar, or network). Computer system 600 may include a display interface 622 that forwards graphics, text, and other data from the communication infrastructure 606 (or from a frame buffer, not shown) for display on the display unit 624 to a user.

Computer system 600 may also include a main memory 604, such as a random access memory (RAM), and a secondary memory 608. The secondary memory 608 may include, for example, a hard disk drive (HDD) 610 and/or removable storage drive 612, which may represent a floppy disk drive, a magnetic tape drive, an optical disk drive, a memory stick, or the like as is known in the art. The removable storage drive 612 reads from and/or writes to a removable storage unit 616. Removable storage unit 616 may be a floppy disk, magnetic tape, optical disk, or the like. As will be understood, the removable storage unit 616 may include a computer readable storage medium having tangibly stored therein (embodied thereon) data and/or computer software instructions, e.g., for causing the processor(s) to perform various operations.

In alternative embodiments, secondary memory 608 may include other similar devices for allowing computer programs or other instructions to be loaded into computer system 600. Secondary memory 608 may include a removable storage unit 618 and a corresponding removable storage interface 614, which may be similar to removable storage drive 612, with its own removable storage unit 616. Examples of such removable storage units include, but are not limited to, USB or flash drives, which allow software and data to be transferred from the removable storage unit 616, 618 to computer system 600.

Computer system 600 may also include a communications interface (e.g., networking interface) 620. Communications interface 620 allows software and data to be transferred between computer system 600 and external devices. Examples of communications interface 620 may include a modem, Ethernet card, wireless network card, a Personal Computer Memory Card International Association (PCMCIA) slot and card, or the like. Software and data transferred via communications interface 620 may be in the form of signals, which may be electronic, electromagnetic, optical, or the like that are capable of being received by communications interface 620. These signals may be provided to communications interface 620 via a communications path (e.g., channel), which may be implemented using wire, cable, fiber optics, a telephone line, a cellular link, a radio frequency (RF) link and other communication channels.

Figure 7:
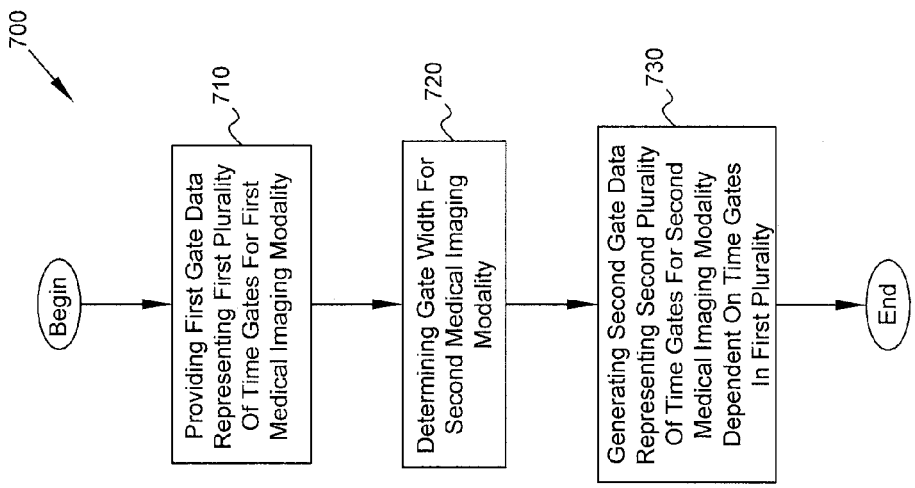
FIG. 7 is a flow diagram of a process in accordance with some embodiments.
Figure 8:
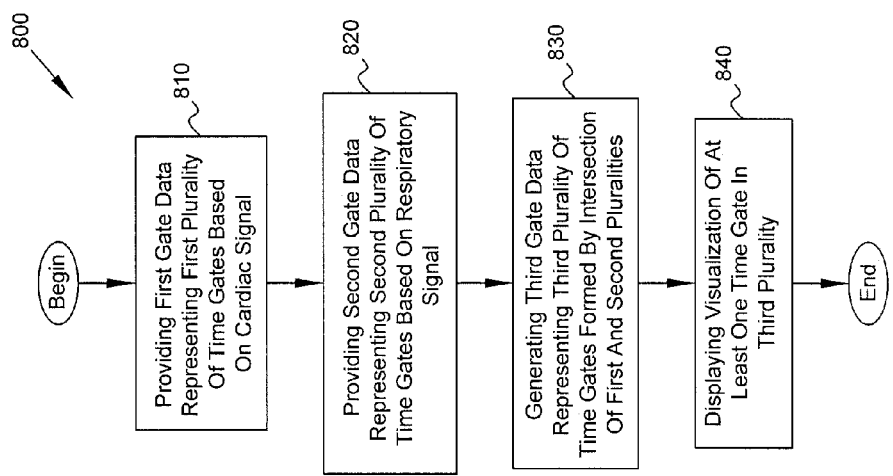
FIG. 8 is a flow diagram of a process in accordance with some embodiments.

FIG. 7 is a flow diagram of a process 700 in accordance with some embodiments. Process 700 includes providing a first gate data representing a first plurality of time gates for a first medical imaging modality (e.g., PET or CT) (block 710). The first plurality of time gates are based on a plurality of cycles of an acquired physiological signal of a person. A gate width is determined for a second medical imaging modality (e.g., CT or PET) (block 720). A second gate data is generated, representing a second plurality of time gates for the second medical imaging modality (block 730). Each time gate in the second plurality of time gates has the determined gate width and is generated dependent on a respective time gate in the first plurality of time gates FIG. 8 is a flow diagram of a process 800 in accordance with some embodiments. Process 800 includes providing a first gate data representing a first plurality of time gates for a medical imaging modality (e.g., PET) (block 810). The first plurality of time gates are based on an acquired cardiac signal of a person. The method further includes providing a second gate data representing a second plurality of time gates for the medical imaging modality (block 820). The second plurality of time gates are based on an acquired respiratory signal of the person. A third gate data is generated, representing a third plurality of time gates formed by an intersection of the first and second pluralities of time gates (block 830). A visualization of at least one of the time gates in the third plurality of time gates is displayed on a screen to a user (block 840).

It is understood by those familiar with the art that techniques described herein may be implemented in hardware, firmware, or software encoded (e.g., as instructions executable by a processor) on a non-transitory computer-readable storage medium.

The apparatuses and processes are not limited to the specific embodiments described herein. In addition, components of each apparatus and each process can be practiced independent and separate from other components and processes described herein.

The previous description of embodiments is provided to enable any person skilled in the art to practice the disclosure. The various modifications to these embodiments will be readily apparent to those skilled in the art, and the generic principles defined herein may be applied to other embodiments without the use of inventive faculty. The present disclosure is not intended to be limited to the embodiments shown herein, but is to be accorded the widest scope consistent with the principles and novel features disclosed herein.

What is claimed is:

1. A method of processing data for medical imaging, the method comprising:
   providing a first gate data representing a first plurality of time gates for a first medical imaging modality, wherein the first plurality of time gates are based on a plurality of cycles of an acquired physiological signal of a person;
   determining a gate width for a second medical imaging modality; and
   generating a second gate data representing a second plurality of time gates for the second medical imaging modality, wherein each time gate in the second plurality of time gates has the determined gate width and is generated dependent on a respective time gate in the first plurality of time gates,
   wherein each time gate in the second plurality of time gates is centered relative to a respective time gate in the first plurality of time gates.

2. The method of claim 1, wherein the physiological signal is a respiratory or cardiac signal.

3. The method of claim 1, further comprising:
   computing, over respective cycles, an average intracycle start time offset for phase-similar time gates in the second plurality of time gates;
   generating a third gate data representing a third plurality of time gates for the second medical imaging modality, wherein each time gate in the third plurality of time gates has the determined gate width and has a gate start time that is offset from a corresponding cycle start time by the average intracycle start time offset; and storing, in a computer memory, a plurality of gate parameters specifying the positions of the third plurality of time gates.

4. The method of claim 3, further comprising receiving an input from a user accepting the second plurality of time gates.

5. The method of claim 4, further comprising:
reconstructing images of the first and second medical imaging modalities by:
applying the first plurality of time gates to first acquisition data obtained from a first scan of the person using the first medical imaging modality,
retrieving the plurality of gate parameters for the third plurality of time gates, and
applying the third plurality of time gates to second acquisition data obtained from a second scan of the person using the second medical imaging modality.

6. The method of claim 5, further comprising generating a fusion image of the first and second imaging modalities based on the first and third pluralities of time gates.

7. The method of claim 1, wherein the first medical imaging modality is one of computed tomography (CT) and positron emission tomography (PET), and the second medical imaging modality is the other of CT and PET.

8. The method of claim 1, further comprising:
in an event that at least two time gates in the second plurality of time gates have the same gate start time, modifying the gate start times of time gates in the second plurality of time gates so that the time gates in the second plurality of time gates all have distinct start times.

9. A non-transitory computer readable medium having instructions embodied tangibly thereupon, the instructions when executed configured to cause one or more processors to perform the operations of:
providing a first gate data representing a first plurality of time gates for a first medical imaging modality, wherein the first plurality of time gates are based on a plurality of cycles of an acquired physiological signal of a person;
determining a gate width for a second medical imaging modality; and
generating a second gate data representing a second plurality of time gates for the second medical imaging modality, wherein each time gate in the second plurality of time gates has the determined gate width and is generated dependent on a respective time gate in the first plurality of time gates,
wherein each time gate in the second plurality of time gates is centered relative to a respective time gate in the first plurality of time gates.

10. The non-transitory computer readable medium of claim 9, wherein the instructions when executed are further configured to cause the one or more processors to perform the operations of:
computing, over respective cycles, an average intracycle start time offset for phase-similar time gates in the second plurality of time gates;
generating a third gate data representing a third plurality of time gates for the second medical imaging modality, wherein each time gate in the third plurality of time gates has the determined gate width and has a gate start time that is offset from a corresponding cycle start time by the average intracycle start time offset; and
storing, in a computer memory, a plurality of gate parameters specifying the positions of the third plurality of time gates.

11. A method of processing data for medical imaging, the method comprising:
providing a first gate data representing a first plurality of time gates for a medical imaging modality, wherein the first plurality of time gates are based on an acquired cardiac signal of a person;
providing a second gate data representing a second plurality of time gates for the medical imaging modality, wherein the second plurality of time gates are based on an acquired respiratory signal of the person;
generating a third gate data representing a third plurality of time gates formed by an intersection of the first and second pluralities of time gates; and
displaying, on a screen to a user, a visualization of at least one of the time gates in the third plurality of time gates.

12. The method of claim 11, further comprising displaying the acquired cardiac and respiratory signals on the screen.

13. The method of claim 12, wherein the acquired cardiac and respiratory signals are displayed as overlaid plots.

14. The method of claim 11, further comprising receiving an input from the user accepting the third plurality of time gates.

15. The method of claim 14, further comprising reconstructing an image using the third plurality of time gates with the medical imaging modality.

16. A non-transitory computer readable medium having instructions embodied tangibly thereupon, the instructions when executed configured to cause one or more processors to perform the operations of:
providing a first gate data representing a first plurality of time gates for a medical imaging modality, wherein the first plurality of time gates are based on an acquired cardiac signal of a person;
providing a second gate data representing a second plurality of time gates for the medical imaging modality, wherein the second plurality of time gates are based on an acquired respiratory signal of the person;
generating a third gate data representing a third plurality of time gates formed by an intersection of the first and second pluralities of time gates; and
displaying, on a screen to a user, a visualization of at least one of the time gates in the third plurality of time gates.

17. The non-transitory computer readable medium of claim 16, wherein the instructions when executed are further configured to cause the one or more processors to receive an input from the user accepting the third plurality of time gates.

18. The non-transitory computer readable medium of claim 17, wherein the instructions when executed are further configured to cause the one or more processors to reconstruct an image using the third plurality of time gates with the medical imaging modality.

* * * * *